(12) United States Patent
Care

(10) Patent No.: US 7,281,407 B2
(45) Date of Patent: Oct. 16, 2007

(54) SENSING FILM MATERIAL

(75) Inventor: Ian C D Care, Derby (GB)

(73) Assignee: Rolls-Royce plc, London (GB)

( * ) Notice: Subject to any disclaimer, the term of this patent is extended or adjusted under 35 U.S.C. 154(b) by 142 days.

(21) Appl. No.: 11/153,424

(22) Filed: Jun. 16, 2005

(65) Prior Publication Data

US 2005/0248356 A1    Nov. 10, 2005

Related U.S. Application Data

(63) Continuation of application No. PCT/GB03/05433, filed on Dec. 12, 2003.

(30) Foreign Application Priority Data

Jan. 11, 2003    (GB)    ............................ 0300664.0

(51) Int. Cl.
  G01N 3/56    (2006.01)
  G01N 19/02    (2006.01)
(52) U.S. Cl. ....................................................... 73/10
(58) Field of Classification Search ..................... 73/10
  See application file for complete search history.

(56) References Cited

U.S. PATENT DOCUMENTS

| | | | |
|---|---|---|---|
| 6,196,057 B1 | 3/2001 | Discenzo | |
| 6,204,656 B1 | 3/2001 | Cheiky-Zelina et al. | |
| 6,525,798 B1 * | 2/2003 | Yamakita et al. | ............ 349/141 |
| 6,756,135 B2 * | 6/2004 | Hasegawa et al. | ........ 428/811.5 |
| 6,938,484 B2 * | 9/2005 | Najafi et al. | ............. 73/514.32 |
| 7,132,723 B2 * | 11/2006 | Park et al. | ................... 257/419 |
| 7,151,582 B2 * | 12/2006 | Yoshida et al. | ............. 349/119 |
| 2003/0046985 A1 | 3/2003 | Schoess | |

FOREIGN PATENT DOCUMENTS

JP    2003214810    7/2003

* cited by examiner

*Primary Examiner*—Hezron Williams
*Assistant Examiner*—Rodney Frank
(74) *Attorney, Agent, or Firm*—W. Warren Taltavull; Manelli Denison & Selter PLLC

(57) ABSTRACT

A sensor 30 has first and second electrodes 32A, 32B spaced to define a gap 34 therebetween. The electrodes are formed on a substrate which can be covered with a film of material. The width of the gap 34 is different at different positions on the electrodes 32. This results in a sensing characteristic which can be made substantially linear, without sensitivity varying with film thickness, which arises from the use of a constant gap width. The sensor can be used to detect or measure film or liquid layer thickness, or solid material deposition.

18 Claims, 6 Drawing Sheets

SENSING FILM MATERIAL

This is a Continuation of International Appln. No. PCT/GB2003/005433 filed Dec. 12, 2003 Which designated the U.S.

FIELD OF THE INVENTION

The present invention relates to sensor arrangements and in particular, arrangements for sensing various properties of films of material.

BACKGROUND OF THE INVENTION

Measurement of a property of a film, such as film thickness, may be required in a variety of situations, such as measurement of the thickness of an oil film within an engine or machine. This measurement can be used to ensure that a lubricating film is adequately thick, or to measure leakage, in the event that the film is formed by leaking fluid. In other situations, measurement may not be required, but merely detection, such as threshold detection when the thickness passes a predetermined value.

Previous proposals for film thickness measurement have included electrodes spaced apart on a substrate. A film of material formed on the substrate therefore bridges the gap between the electrodes. Voltages applied to the electrodes allow measurements of resistance and capacitance across the gap. These values will change with changes in film thickness. However, previous proposals have been found prone to saturation in their response characteristics as film thickness increases, and have thus been limited in their usefulness.

SUMMARY OF THE INVENTION

According to the present invention, there is provided a sensor for sensing a property of a film of material, the sensor comprising first and second electrodes spaced to define a gap therebetween, the film of material being located within the gap, during use, wherein the width of the gap is different at different positions on the electrode members whereby the sensing characteristics of the sensor are different at different positions on the electrode members.

Preferably the width of the gap varies substantially continuously. Alternatively, the width of the gap may change in step fashion at one or more discontinuities. The width of the gap preferably varies to create a substantially linear output characteristic for the sensor, in response to changes in the property being sensed.

The electrodes may be generally elongate. The electrodes may be interdigitated fingers, the gap width being different at different positions along each finger. The interdigitated fingers may form a repeating pattern.

Alternatively, the electrodes may be generally curved to define a curved gap therebetween. The electrodes may form inner and outer closed curves, the gap forming a continuous curve therebetween.

The thickness of one electrode may be different at different positions on the electrode.

The electrodes may be mounted to be adjustably positioned relative to one another, to allow the gap widths to be changed.

Preferably, the sensor further comprises a voltage source operable to apply a voltage to the electrodes, across the gap, and control means operable to sense the response to the applied voltage and to deduce the film property therefrom. Preferably the voltage source is operable at a plurality of frequencies, and the control means is operable to sense the response at each frequency. Preferably the or one of the operating frequencies of the voltage source is DC. The control means is preferably operable to combine sensed responses to eliminate at least one frequency-dependent component of the property being sensed. The control means may be operable to sense one or more of the resistance, reactance, capacitance, conductance or impedance between the electrodes.

In another aspect, the invention provides a machine incorporating a sensor as aforesaid.

The sensor may be formed at a surface of the machine, the film of material being on the surface, during use of the machine, whereby the sensor is covered by the film, which spans the gap.

BRIEF DESCRIPTION OF THE DRAWING

Examples of the present invention will now be described in more detail, by way of example only, and with reference to the accompanying drawings, in which.

DETAILED DESCRIPTION OF THE INVENTION

Figure 1:
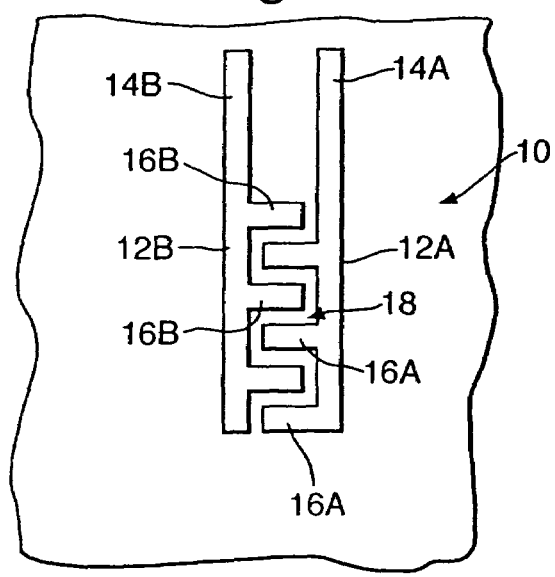
FIG. 1 is a schematic view of a sensor according to a previous proposal.

FIG. 1 illustrates a previous proposal for a sensor 10 for sensing a property of a film of material, such as film thickness. The sensor 10 is in the form of two electrodes 12A, 12B formed, for example, by metal deposition on an insulating substrate. Each electrode has a lead segment 14A, 14B continuous with a series of fingers 16A, 16B. The fingers 16 of the electrodes 12 are interdigitated so that a serpentine gap 18 of constant width is formed therebetween.

In use, a film of material, such as oil, covers the sensor 10. It is found that electrical properties measured between the electrodes 12 will vary in dependence on the thickness of the film on the sensor 10. Various electrical properties can be measured by application of voltages between the electrodes 12, and therefore across the gap, such as resistance, reactance, capacitance or impedance.

Figure 2:
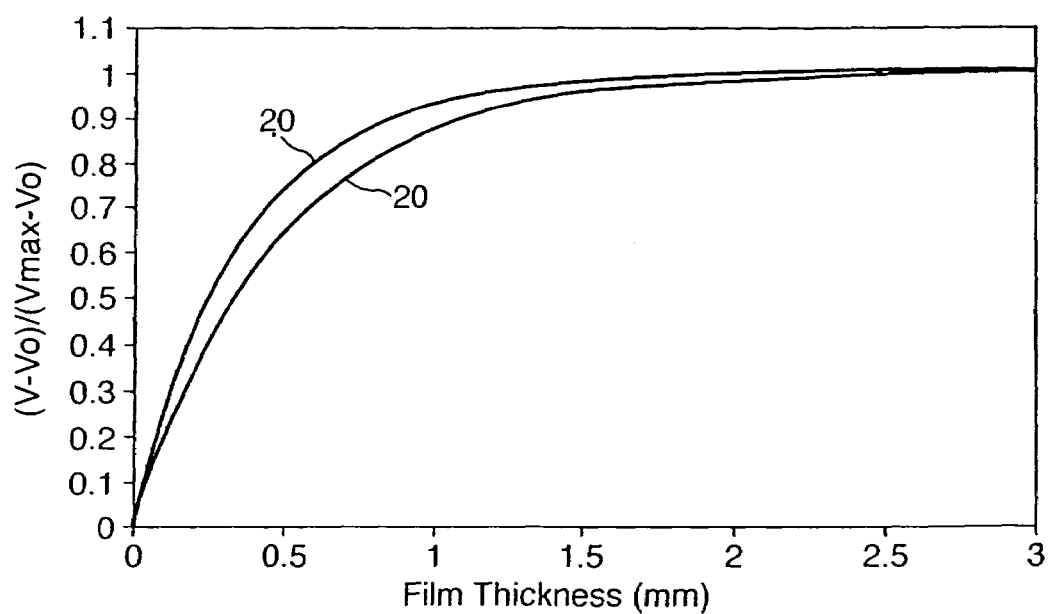
FIG. 2 is a plot of the response characteristic of a sensor like that of FIG. 1.

FIG. 2 is a plot of two output characteristics typical of sensors of the type shown in FIG. 1. The two different characteristics 20 are for different gap widths. The plots in FIG. 2 relate film thickness (horizontal axis) and a normalised voltage value, effectively indicating the capacitance (vertical axis). It can readily be seen that the characteristics 20 are similar in form and are significantly non-linear. In each case, the illustrated characteristics would have an effective upper limit on film thickness for accurate measurement, at about 1 mm, although measurements could be taken up to about 1.5 mm thickness. Linearity ceases at about 0.4 mm. At greater thicknesses, the output characteristic of the devices has saturated and further useful information cannot be retrieved. That is, a further increase in film thickness results in no perceptible increase in capacitance. Similarly, a measurement of resistance across the gap will also saturate.

Characteristics of this general form, in particular exhibiting saturation, are typical of sensor geometries which, like FIG. 1, have a constant gap between the electrodes. The upper characteristic is for the narrower of the gaps, showing that a narrow gap will saturate sooner than a wide gap.

Figure 3:
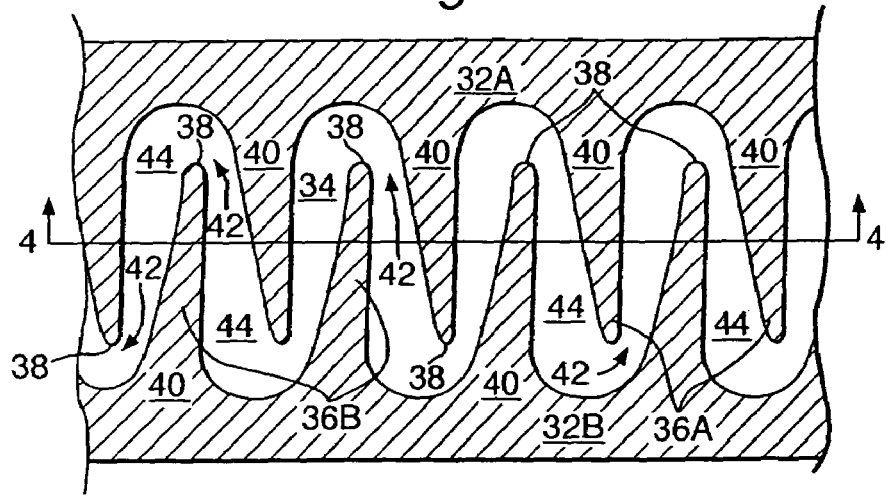
FIG. 3 is a schematic view of a first sensor in accordance with the present invention.

FIG. 3 shows a sensor 30 in accordance with the present invention. The sensor 30 has first and second electrodes 32A, 32B spaced to define a gap 34 therebetween. The electrodes 32 are formed on a substrate which can be covered with a film of material, such as oil, to cover the sensor 30, spanning the gap between the electrodes 32.

Unlike the sensor 10 of FIG. 1, it can be seen from FIG. 3 that the width of the gap 34 is different at different positions on the electrodes 32. This results in the sensing characteristic of the sensor being different at different positions on the electrodes 32.

In more detail, the electrodes 32 each have fingers 36A, 36B which are interdigitated. Unlike the fingers 16 of FIG. 1, the fingers 36 are not simple rectangles, but have a curvi-linear, tapering form, being narrowest at their tips 38. Each tip 38 closely approaches the root region 40 of a finger 36 on the other electrode 32, so that the gap 34 is at its narrowest between each tip 38 and the corresponding root region 40. This narrowest region of the gap 34 is indicated at 42 in FIG. 3.

The separation of each tip 38 from the root region 40 of the next neighbouring finger 36 on the other electrode 32 is much greater, as indicated at 44 and indeed, in the geometry of FIG. 3, the separation at 44 represents the widest part of the gap 34.

It can be seen that the geometry of the electrodes 32 forms a repeating pattern along the sensor 30, which contrasts with the pattern of the electrodes 52, which does not precisely repeat along the sensor 50, there being a narrower gap at some positions than at others.

Figure 4:
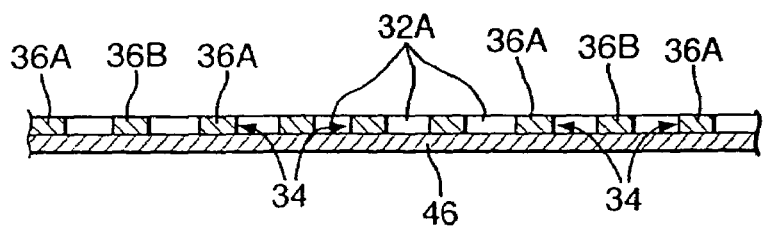
FIG. 4 is a section along the line 4-4 in FIG. 3.

Electrodes 32 of the form shown in FIG. 3 can be formed by various techniques on a substrate, as illustrated in FIG. 4. A substrate 46 carries the electrodes 32 and their fingers 36A, 36B. The substrate 46 may be part of the sensor 30 and used for mounting the sensor in position, or the electrodes 32 may be formed directly on an existing surface at the measurement position. It is found that the sensitivity of the sensor 30 improves if the substrate 46 is a good insulator and has a poor capacitive dielectric. Ceramic or PTFE substrates have been found useful. Circuit boards having electrodes formed from an etched copper layer on a base of a plastics material have been found satisfactory. In some applications, electrodes may be formed directly on a surface provided by an existing component of the machine, for example to measure lubrication films on that surface, in which case that surface should again preferably be a good insulator with a poor capacitive dielectric. Flexible substrates could be used, such as polythene, to allow the sensor to be attached to a non-flat surface, such as the curved surface within a bearing chamber or the like. In any particular situation, the final choice of materials will depend on the electrical characteristics required of the sensor, and on physical or chemical characteristics, such as the nature of the film to be sensed, and its interaction with the materials chosen for the sensor. For example, engine oil may react with copper electrodes, damaging a sensor based on copper electrodes.

In use, the sensor 30 is covered by a film of material, such as an oil. Measurement may take place by applying voltages across the electrodes. The response of the sensor 30 is more complex than shown in FIG. 2. This arises because the sensing characteristic of the gap 34 will saturate at different film thicknesses at different positions, by virtue of the gap 34 having a non-constant width. It is found that in constant width designs (FIG. 1), a narrow gap will saturate at a smaller film thickness than a wider gap. Consequently, the output characteristic of a non-constant gap sensor 30 will tend to be dominated by the performance of the narrow regions 42. Consequently, the geometry of the sensor 30 is preferably chosen so that the narrow gap 42 extends over only a relatively short length of the finger. The output characteristic is also dependent on the nature of the film being measured. Appropriate design of the geometry of the fingers is found to allow the sensor 30 to be designed to have an output characteristic which is substantially linear with film thickness over a much greater range of film thicknesses than in previous designs which use a constant gap width.

Figure 5A:
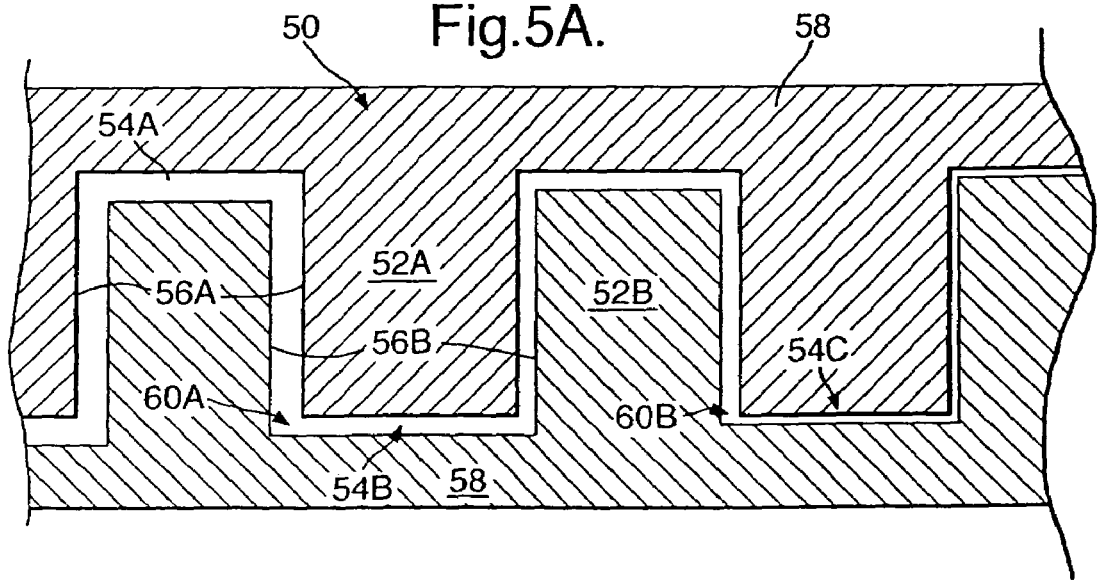
FIGS. 5A and 5B correspond with FIG. 3, showing further examples of sensors in accordance with the present invention.

Further consideration of FIG. 3 shows that the width of the gap 34 varies substantially continuously, without discontinuities. This is particularly useful for measurement applications, where a precise value for film thickness is required. In other situations, detection, particularly threshold detection may be required without precise measurement. For such applications, it may be more desirable to provide a geometry in which the width of the gap changes in step fashion at one or more discontinuities. An example is shown in FIG. 5A. The sensor 50 of FIG. 5A is formed by electrodes 52A, 52B which define a gap 54 between them. Each electrode 52 has fingers 56A, 56B projecting from a base 58 toward the other electrode 52, so that the fingers 56 are interdigitated. Each finger 56 is generally rectangular in form, but the fingers 56 are not all of the same size. The shape, size and position of the fingers 56 creates gap portions 54A, 54B and 54C of different width, separated by discontinuities, such as at 60A, 60B, where the width of the gap 54 undergoes a step change in width. Thus, a first gap portion 54A is relatively wide and is separated by discontinuity 60A from a gap portion 54B of intermediate width, which is in turn separated by discontinuity 60B from a narrow gap portion 54C.

Figure 5B:
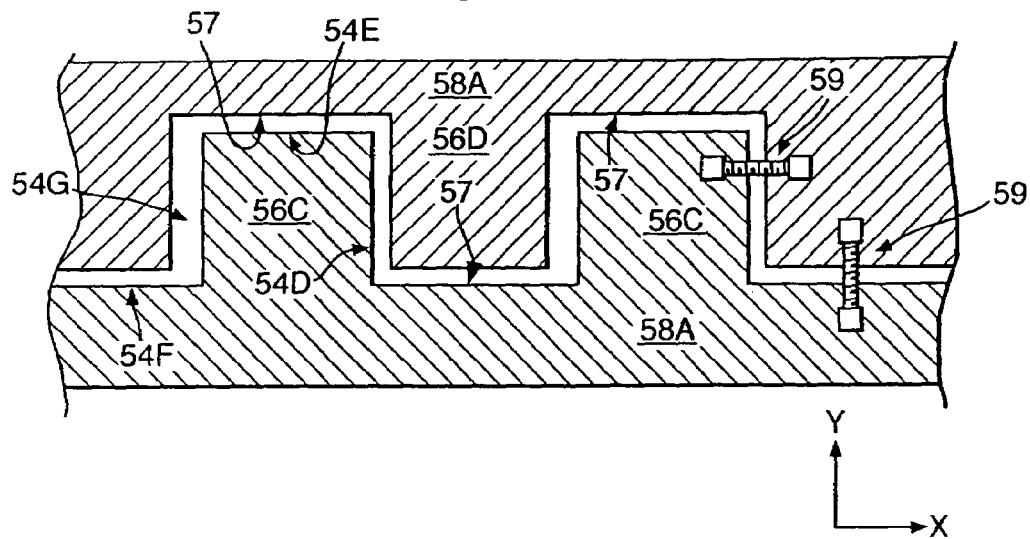

FIG. 5B shows a further alternative. In this case, electrodes 58A have a castellated shape generally similar to that of the electrodes 58 in FIG. 5. However, there are some important differences in the geometry. These can best be explained by reference to the X and Y axes indicated in FIG. 5B. Thus, each finger 56C, 56D extends into a space 57 in the other electrode 58A. The width (in the X direction) of the finger 56C, 56D is less than the width (in the X direction) of the space 57. The length (in the Y direction) of the finger 56C, 56D is greater than the depth (in the Y direction) of the space 57. The width (in the X direction) of the fingers 56C is different to the width (in the X direction) of the fingers 56D. The length (in the Y direction) of the fingers 56C is different from the length (in the Y direction) of the fingers 56D. Consequently, when the two electrodes 58A are brought together as shown in FIG. 5B, four different gap widths are created, indicated at 54D, 54E, 54F and 54G. Furthermore, relative movement (by translation) of one electrode 58A relative to the other, in the X or Y direction serves to vary the width of at least two of these gaps, so that various combinations of four gap sizes can be chosen, which has the effect of tuning the sensor, as will become apparent. The gap widths can be selected when the electrodes are placed permanently in their relative positions or alternatively, control arrangements, such as screw threads 59, may be provided to allow gap widths to be adjusted during setting up and calibration, or to be changed for different applications.

In addition to the castellated forms of FIGS. 5A and 5B, other interfitting shapes could be used, with triangular or curved finger shapes, for example. In use, a sensor 50 having discontinuities as described, is particularly useful for threshold detection.

As film thickness increases, each of the gap portions 54 will saturate in turn, beginning with the narrowest gap portion 54C. Each gap has an equivalent circuit of a parallel resistor and capacitor pair, and each gap is in parallel with the others. Consequently, the output characteristic of the sensor will exhibit a discontinuity whenever one of the gap portions 54 saturates. Detecting these discontinuities in the output characteristic readily allows a determination to be made as to the range within which the film thickness is currently lying, even without precise calibration and measurement. Thus, by detecting discontinuities, the film thickness can be detected as being between the thickness at which one gap portion 54 saturates, and the thickness at which the next-to-saturate cap portion will saturate.

Figure 6A:
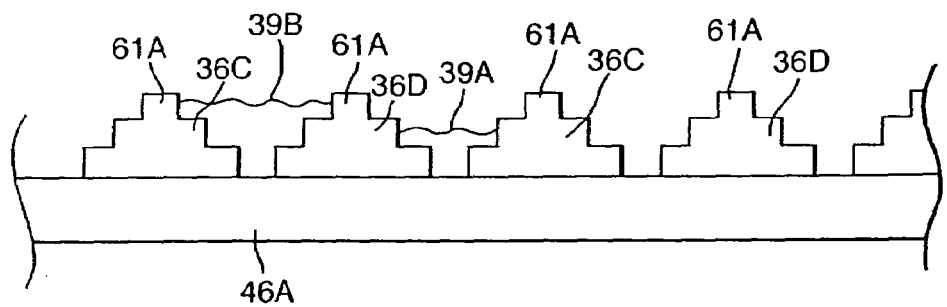
FIGS. 6A and 6B are sections showing examples in which electrode height varies.
Figure 6B:
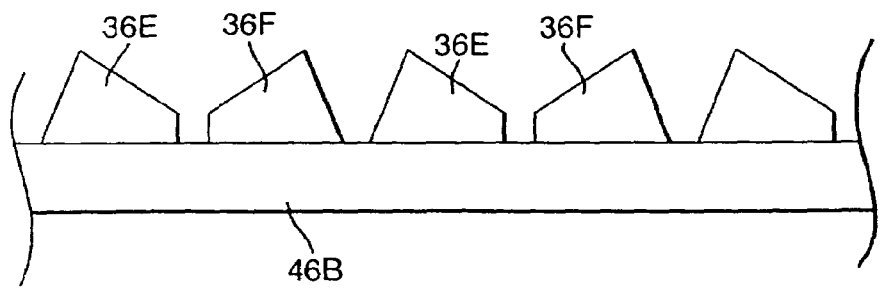

The electrode geometries described above are all of a generally planar form, and do not make use of the dimension perpendicular to the plane, when setting gap widths. FIGS. 6A and 6B show two examples of how this dimension can be used.

FIG. 6A shows a substrate 46A on which interdigitated electrode fingers 36C, 36D are formed. Thus, alternate fingers 36C are interconnected to form one electrode; fingers 36D are interconnected to form the second electrode. The gap between the electrodes, for sensing, is thus provided between the adjacent fingers 36C, 36D.

FIG. 6A shows fingers 36C, 36D which have a stepped cross-section. Consequently, at the base of the electrodes 36C, 36D, adjacent the substrate 46A, the electrodes 36C, 36D are at their widest and the gaps between adjacent electrodes are at their narrowest. The electrodes 36C, 36D rise to peaks 61A at which they have least width, so that the gap between adjacent electrodes has the greatest width. Between these extremes, the gap between adjacent electrodes varies in step-wise fashion in width, as can clearly be seen in FIG. 6A. Consequently, as a film forms on the substrate 46A, between the fingers 36C, 36D, the relatively narrow valleys between the bases of adjacent fingers 36C, 36D will first be filled, so that the thin film is sensed initially by a relatively narrow gap. As the film thickness increases, the valley will be filled past each step of the profile, in turn, thereby saturating a gap width, and beginning to fill the next portion of the gap, with greater width. Reference numeral 39A illustrates an intermediate film thickness, for which an intermediate sensor gap width is effective. As thickness approaches the maximum thickness prior to total saturation of the device, the maximum width of the gap, between the peaks 61A, will be effective in sensing, with the film thickness at a level indicated at 39B in FIG. 6A.

It is to be understood that the illustration of two different levels 39A, 39B on FIG. 6A is schematic only. In practice, it is to be expected that the same film thickness would be present between each adjacent pair of fingers 36C, 36D.

The output characteristic of a sensor constructed in accordance with FIG. 6A will exhibit discontinuities as described above in relation to FIGS. 5A and 5B, as the film thickness reaches each step in the fingers, the gap below the step saturates, and the gap above the step begins to fill.

In an alternative arrangement shown in FIG. 6B, continuous variations in the height of fingers is used to remove these discontinuities. In FIG. 6B, interdigitated electrodes 36E, 36F are formed on a substrate 46B, generally in the manner previously described, with fingers 36E interconnected to form one electrode and fingers 36F interconnected to form the other electrode. The fingers 36E, 36F have sloping upper surfaces so that the gap width between fingers 36E, 36F varies continuously, over ranges of film thickness, rather than in the step-wise fashion of the arrangement of FIG. 6A. In FIG. 6B, the upper surfaces of the fingers 36E, 36F are straight, so that the gap width will change in generally linear fashion, but other shapes could be used to provide more complex variation of gap width with film thickness, allowing the output characteristic of the sensor to be controlled.

Features of the arrangements of FIG. 6A and FIG. 6B can be used in various combinations. For example, finger shapes could be designed to provide some ranges of film thickness over which the gap width changes without discontinuities, and other film thicknesses at which the gap width changes at a discontinuity. The gap between each adjacent pair of fingers may have the same shape, as shown in FIG. 6A, arising from a symmetry of the finger profiles, or the finger profiles may be assymetric, as shown in FIG. 6B, so that alternating gap shapes are created. In addition, variation of finger thickness, as described in relation to FIGS. 6A and 6B, can be used in conjunction with arrangements described in relation to other drawings of this specification, providing a wide range of possible combinations of factors governing the gap width experienced at each film thickness, and thus governing the sensor output characteristic.

Figure 7:
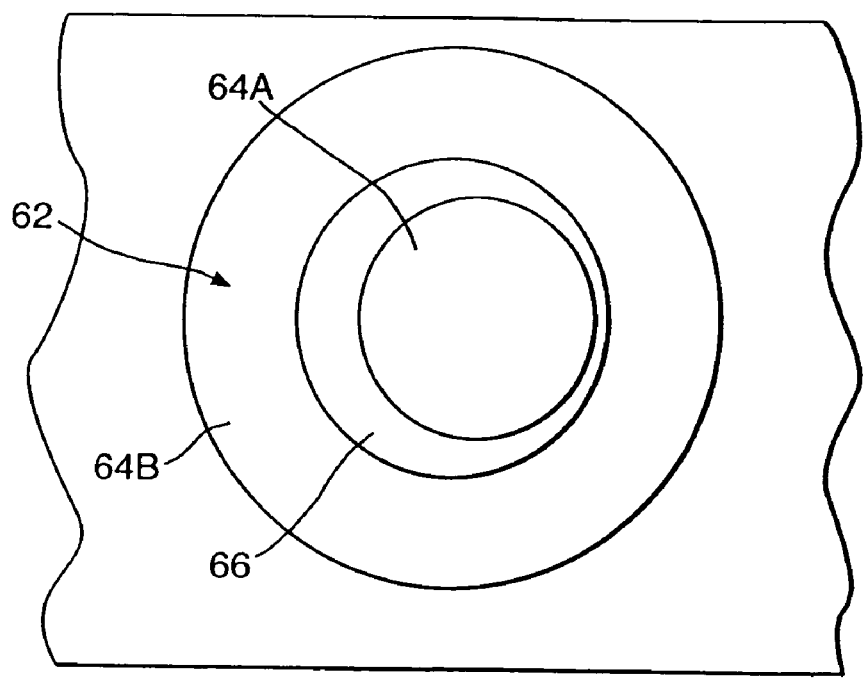
FIGS. 7, 8A, 8B and 8C correspond with FIG. 3, showing further examples.

The electrode geometries described above all use generally elongate electrodes, being described as having fingers, for example. Furthermore, a row of interdigitated fingers will extend over a significant area of the substrate, so that the sensor output will provide, in effect, an averaged value over the whole area. In some circumstances, it is desirable to be able to take spot measurements at relatively well defined and small locations. FIGS. 7 and 8 illustrate two geometries by which this can be achieved.

FIG. 7 illustrates a sensor 62 which has inner and outer electrodes 64A, 64B defining a gap 66 therebetween. In this example, the inner electrode 64A is circular and lies within electrode 64B, which forms a circular ring. However, the electrodes 64A, 64B are not concentric. That is, the electrode 64A is off-centre relative to the electrode 64B, so that the width of the gap 66 is not constant at all positions around the electrode 64A. The circular shape of both electrodes 64 results in the width of the gap varying substantially continuously around the electrodes, allowing measurement to be effected in the manner described above in relation to FIG. 3.

Various alternative shapes could be used instead of those shown in FIG. 7. For example, one or both of the electrodes 64 need not be circular. The edges of the electrodes 64 could be curved with other curved shapes, such as spirals, ellipses or the like.

Figure 8A:
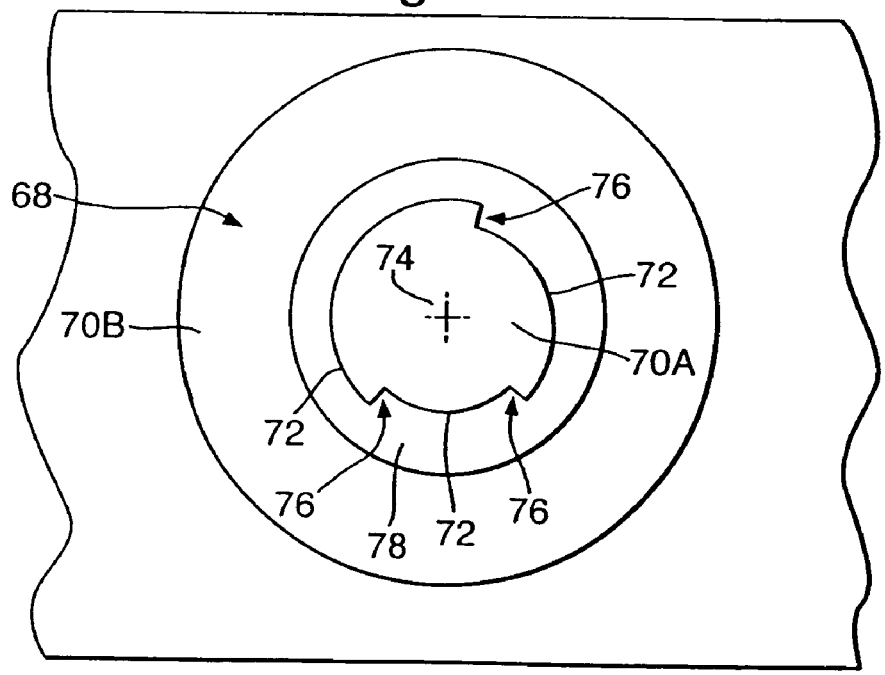

In a further alternative, particularly intended for detection, such as threshold detection, generally curved electrodes could be used to define a gap which has discontinuities, as shown in FIG. 8A. FIG. 8A shows a sensor 68 formed by inner and outer electrodes 70A, 70B. In this example, the outer electrode 70B is a circular ring. The inner electrode 70A has a more complex shape. The outline has a series of circular portions 72, each centered at a common centre 74 which is concentric with the outer electrode 70B. The circular portions 72 meet at discontinuities 76, which form radial steps around the electrodes 70A. Consequently, the width of the gap 78 between the electrodes 70A, 70B changes in step fashion at each discontinuity 76. The region of the sensor 68 between each neighbouring pair of discontinuities 76 will therefore saturate at different film thicknesses, allowing threshold detection to be achieved, as described above.

Figure 8B:
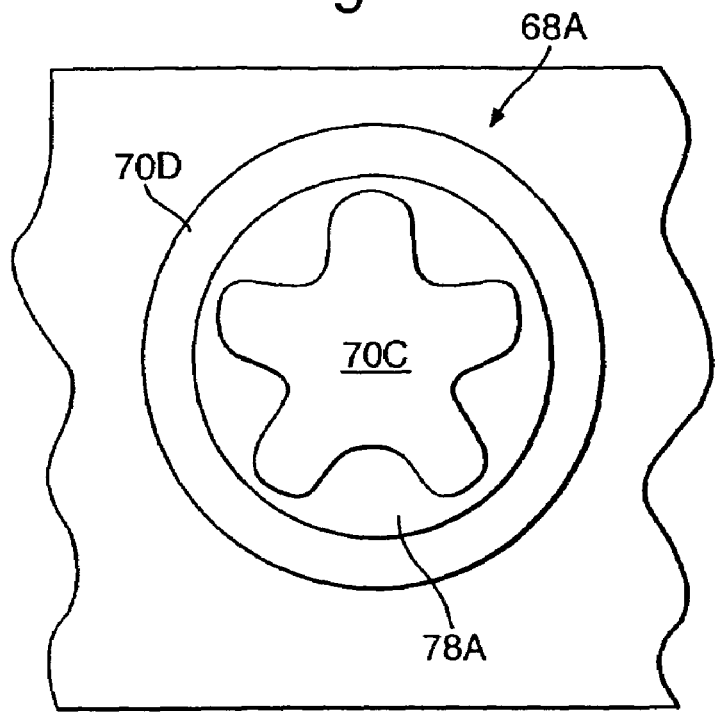

FIG. 8B shows an alternative sensor 68A formed by inner and outer electrodes 70C, 70D. In this example, the outer electrode 70D is again a circular ring. The inner electrode 70C has a multi-pointed star shape. Consequently, the width of the gap 78A between the electrodes 70C, 70D varies substantially continuously around the ring.

Figure 8C:
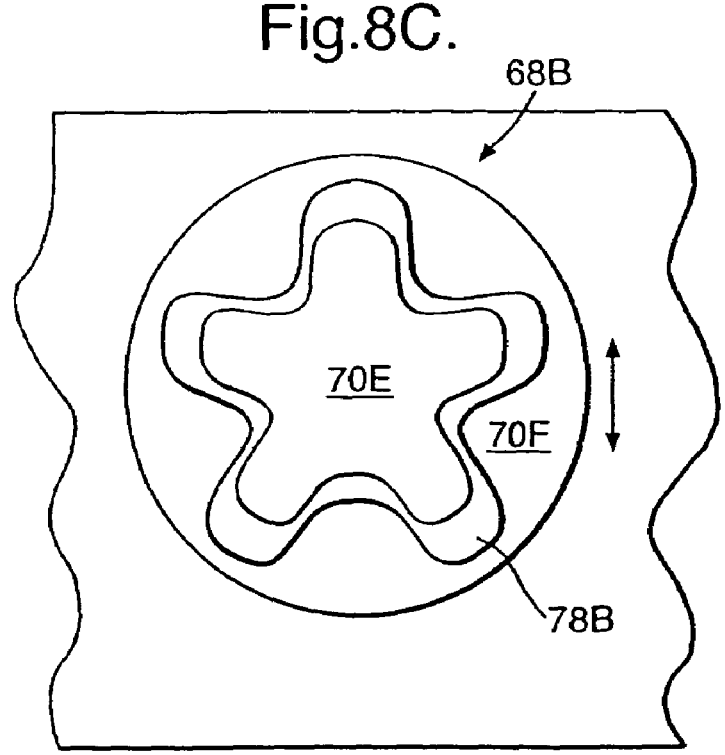

FIG. 8C shows a further alternative sensor 68B, formed by inner and outer electrodes 70E, 70F. In this example, the inner electrode 70E again has a multi-pointed star shape similar to that of the electrode 70C. The outer electrode 70F is not a circular ring, but has a similar star shape along its inner edge. Thus, the width of the gap 78B again varies substantially continuously around the electrodes, in a more complex manner than in the examples of FIGS. 8A and 8B. The gap widths can be adjusted by rotating the electrodes 70E, 70F relative to each other, either as part of set-up or calibration, or to change the sensor characteristic for different applications or materials.

In the examples of FIGS. 7, 8A, B and C the circular or quasi-circular nature of the sensor provides a relatively long gap within a relatively small area, thus providing a form of spot sensor.

Figure 9:
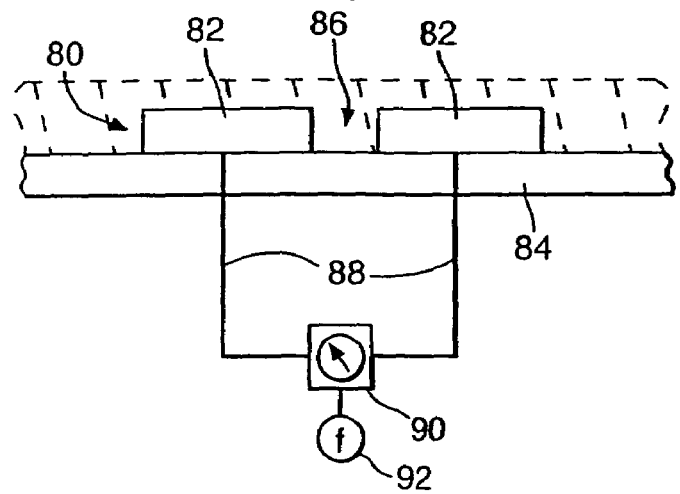
FIG. 9 is a schematic diagram of the connection of a sensor to a voltage source, in accordance with the present invention.

FIG. 9 schematically shows an example of an arrangement for using any of the sensors of FIGS. 3 to 8. FIG. 9 illustrates a generalised form of sensor 80, which may have the form of any of FIGS. 3 to 8 or the alternatives described above. Electrodes 82 are mounted on a substrate 84 to provide a gap 86 between them, and are electrically connected at 88 to a measuring device 90 which is in turn associated with a variable frequency oscillator 92. The oscillator 92 and device 90 serve to take measurements from the electrodes 82 such as resistance, reactance, capacitance, conductance or impedance between the electrodes 82, at a frequency which can be set by the oscillator 92. Consequently, measurements can be taken from the sensor 80 at more than one frequency. Preferably, the oscillator 92 is operable at DC (i.e. a frequency of 0 Hz) and at least one other frequency. Alternatively, the oscillator 92 may be operable at three or more different frequencies, which may include DC. The processing of these values may serve to eliminate one or more variable of the film being sensed, such as temperature or incident light excitation.

Figure 10:
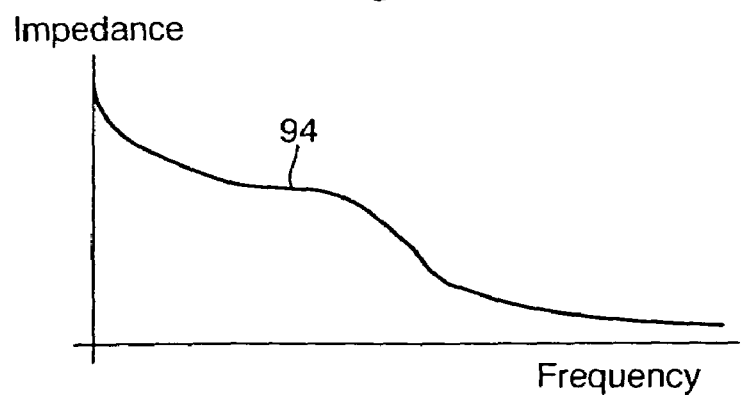
FIG. 10 illustrates a frequency-dependent response characteristic of a sensor of the invention.

FIG. 10 illustrates a typical capacitive response of electrodes of the type under discussion, showing frequency (horizontal axis) and measured impedance (vertical axis). The characteristic 94 in FIG. 10 is drawn for a constant film thickness and constant temperature. At different film thicknesses or different temperatures, a different characteristic will be measured. Consequently, measurement at several different frequencies (desirably at least three) will allow the appropriate characteristic pertaining to the current conditions to be identified and to measure the temperature or to eliminate temperature from the results, by appropriate calculation.

Figure 11:
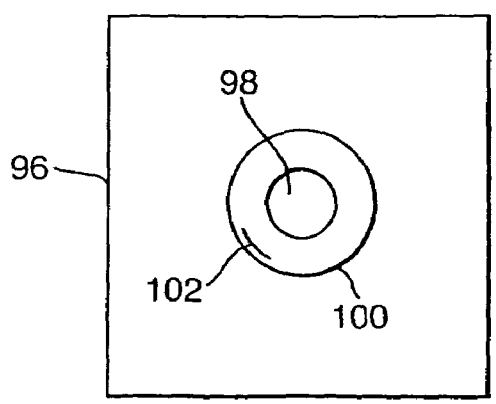
FIG. 11 illustrates an example of the manner of use of a sensor of the invention.

FIG. 11 illustrates, highly schematically, a sensor of the type described above, incorporated into a machine 96. In this example, the machine 96 has a shaft 98 which turns in a bore 100. Lubrication material (not shown) forms a film around the shaft 98 within the bore 100. A sensor in accordance with the invention is formed on the wall of the bore, either by attaching a substrate carrying electrodes, or by directly attaching electrodes to the bore wall. Consequently, lubricant within the bore 100 will form a layer over the sensor 102. The sensor 102 can be used in the manner described above to measure the film thickness of lubricant, allowing lubrication to be monitored, for example by transmitting the output of the sensor to a remote location for recordal or display. Alternatively, the sensor 102 may be on a rotating member (such as a shaft), with the output signals from the sensor being extracted by suitable means, such as telemetry.

The examples illustrated above have all used geometries in which the sensing gap is a space geometrically located between the electrodes and into which the film material is introduced. However, there is a larger volume within which film material can electrically influence the electrodes and it is the properties of this electrical gap which are relevant to the present invention. Thus, the film material could be provided at a location which is electrically within the gap between the electrodes (i.e. is having an electrical influence on the electrodes), but is outside the gap when defined from strict geometry. Thus, it is envisaged that a sensor could be built with electrodes embedded wholly within a sensor surface, so that film material formed on the surface does not penetrate the surface to be geometrically located between the electrodes, but nevertheless can be sensed by virtue of its electrical influence. Thus, film material can be considered to be located within the electrical gap between the electrodes, even if not within the geometric gap. Many alternative arrangements could be devised for making use of this further possibility.

The above examples have all made reference to film thickness as the property being sensed. Other properties can be sensed in similar manner. For example, using a film thickness which is beyond the saturation point of the sensor, so that the sensor remains fully saturated regardless of film thickness, allows other properties of the film to be measured, such as the presence of contaminants, rust particles etc. in the lubricant. Alternatively, film properties may be measured by measuring capacitance and resistance from the same sensor. Appropriate processing of the results allows the effect of film thickness to be removed from the results, to derive information about film properties, such as the condition of a lubricant. A sensor could be used as a fluid leak detector, particularly when designed with discontinuities, for threshold detection, as described above. For example, the sensor could be located to be covered by a film in the event of a leak, and then used for threshold detection to determine whether or not a film is present, and thus to indicate a leak. The sensor could also be used to provide feedback, for example for controlling position within a lubricated bearing.

The examples above have made reference to liquid films, particularly oil or other lubricants. Other films could be measured, such as films formed by material deposition, such as wall lacquer and coking within an engine. Sensors could be used in manufacture, such as to detect the presence of, or measure, a film of material such as a plastics film in an extrusion or moulding process.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A film thickness sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members.

2. A sensor according to claim 1, wherein the width of the gap varies substantially continuously.

3. A sensor according to claim 1, wherein the width of the gap changes in step fashion at one or more discontinuities.

4. A sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members, wherein the width of the gap varies to create a substantially linear output characteristic for the sensor, in response to changes in the property being sensed.

5. A sensor according to claim 1, wherein the electrodes are generally elongate.

6. A sensor according to claim 1, wherein the electrodes are interdigitated fingers, the gap width being different at different positions along each finger.

7. A sensor according to claim 6, wherein the interdigitated fingers form a repeating pattern.

8. A sensor according to claim 1, wherein the electrodes are generally curved to define a curved gap therebetween.

9. A sensor according to claim 8, wherein the electrodes form inner and outer closed curves, the gap forming a continuous curve therebetween.

10. A sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members wherein the thickness of at least one electrode is different at different positions on the electrode.

11. A sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members, wherein the electrodes are mounted to be adjustably positioned relative to one another, to allow the gap widths to be changed.

12. A sensor according to claim 1, further comprising control means operable to take measurements from the electrodes, across the gap, and to deduce the film property therefrom.

13. A sensor according to claim 12, wherein the control means is operable at a plurality of frequencies.

14. A sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members wherein the sensor further comprises control means operable to take measurements from the electrodes, across the gap, and to deduce the film property therefrom wherein the control means is operable at a plurality of frequencies, wherein the or one of the operating frequencies of the voltage source is DC.

15. A sensor for sensing a property of a film of material, the sensor comprising first and second electrodes spaced to define a gap therebetween, the film of material being located within the gap, during use, characterised in that the width of the gap is different at different positions on the electrode members whereby the sensing characteristics of the sensor are different at different positions on the electrode members wherein the sensor further comprises control means operable to take measurements from the electrodes, across the gap, and to deduce the film property therefrom wherein the control means is operable at a plurality of frequencies, wherein the control means is operable to combine measurements to eliminate at least one frequency-dependent component of the property being sensed.

16. A sensor according to claim 1, wherein the control means is operable to sense one or more of the resistance, reactance, capacitance, conductance or impedance between the electrodes.

17. A machine incorporating a sensor as claimed in claim 1.

18. A machine according to claim 17, wherein the sensor is formed at a surface of the machine, the film of material being on the surface, during use of the machine, whereby the sensor is covered by the film, which spans the gap.

* * * * *